(12) United States Patent
Rademacher et al.

(10) Patent No.: US 7,615,235 B2
(45) Date of Patent: *Nov. 10, 2009

(54) FILM-SHAPED OR WAFER-SHAPED PHARMACEUTICAL PREPARATION WITH MASKED TASTE

(75) Inventors: Tina Rademacher, Bad Breisig (DE); Frank Seibertz, Rheinbrohl (DE); Petra Brandt, Pinneberg (DE); Christian Von Falkenhausen, Meckenheim (DE); Markus Krumme, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 578 days.

This patent is subject to a terminal disclaimer.

(21) Appl. No.: 10/505,317

(22) PCT Filed: Feb. 4, 2003

(86) PCT No.: PCT/EP03/01052

§ 371 (c)(1),
(2), (4) Date: Aug. 20, 2004

(87) PCT Pub. No.: WO03/070227

PCT Pub. Date: Aug. 28, 2003

(65) Prior Publication Data

US 2005/0163830 A1 Jul. 28, 2005

(30) Foreign Application Priority Data

Feb. 21, 2002 (DE) .............................. 102 07 394

(51) Int. Cl.
*A61F 13/00* (2006.01)
*A61F 2/00* (2006.01)
*A61K 9/68* (2006.01)
*A61K 47/00* (2006.01)

(52) U.S. Cl. .................. 424/441; 424/422; 424/428; 424/434; 424/435; 424/439

(58) Field of Classification Search .................. None
See application file for complete search history.

(56) References Cited

U.S. PATENT DOCUMENTS

| 4,184,888 A | * | 1/1980 | Zoumut ................... 106/184.1 |
| 4,639,368 A | | 1/1987 | Niazi et al. |
| 5,800,832 A | * | 9/1998 | Tapolsky et al. ............ 424/449 |
| 5,869,098 A | * | 2/1999 | Misra et al. ................. 424/484 |
| 6,150,424 A | | 11/2000 | Breitenbach et al. |
| 6,287,596 B1 | * | 9/2001 | Murakami et al. .......... 424/464 |
| 2001/0006677 A1 | | 7/2001 | McGinity et al. |
| 2003/0091629 A1 | * | 5/2003 | Pather et al. ................ 424/466 |
| 2004/0028732 A1 | * | 2/2004 | Falkenhausen et al. ...... 424/468 |
| 2006/0057207 A1 | * | 3/2006 | Ziegler et al. ............... 424/484 |
| 2007/0122455 A1 | * | 5/2007 | Myers et al. ................ 424/439 |

FOREIGN PATENT DOCUMENTS

| DE | 196 35 676 A1 | 3/1998 |
| GB | 1226821 | 3/1971 |
| WO | WO 99/37308 | 7/1999 |
| WO | WO 02 02085 A2 * | 1/2002 |

* cited by examiner

*Primary Examiner*—S. Tran
(74) *Attorney, Agent, or Firm*—D. Peter Hochberg; Sean F. Mellino; Daniel J. Smola

(57) ABSTRACT

The invention relates to thin film-shaped or wafer-shaped pharmaceutical preparations for oral administration of active substances. The preparations contain at least one matrix-forming polymer which has at least one active substance and at least one carbon dioxide-forming substance dissolved or dispersed therein.

28 Claims, No Drawings

FILM-SHAPED OR WAFER-SHAPED PHARMACEUTICAL PREPARATION WITH MASKED TASTE

CROSS REFERENCE TO RELATED APPLICATIONS

This application is a National Stage application of International Application No. PCT/EP03/01052, filed Feb. 4, 2003, which claims priority of German Application No. 102 07 394.5, filed Feb. 21, 2002.

FIELD OF THE INVENTION

The invention relates to thin, film-shaped or wafer-shaped, orally applied active substance preparations for administration of active substances, preferably of pharmaceutical active substances. With these preparations, the active substances are preferably administered via the oral mucosa. Where the active substance preparations are swallowed, the active substances are released in the stomach and/or the intestine.

DESCRIPTION OF THE PRIOR ART

With conventional administration forms, e.g. tablets, which disintegrate and release the active substance in the stomach, the onset of action of the pharmaceutical product as a rule occurs only with a considerable delay in time. Although in the case of tablets that already disintegrate in the mouth and whose active substance is absorbed via the oral mucosa, this disadvantage is alleviated. However, it has to be taken into consideration that a considerable portion of the active substance preparation reaches the stomach with the saliva and is therefore not available for the quick absorption via the oral mucosa. In addition, following gastrointestinal absorption of the active substance the active substance is relatively quickly catabolized in the liver (i.e., the "first pass effect").

For these and other reasons, thin administration forms, such as film-shaped or wafer-shaped preparations, are advantageous. The small thickness, compared to the surface area, results in a short diffusion path when such a form of medicament is applied to the oral mucosa. This leads to a quick release of the active substance, which can be rapidly absorbed directly through the oral mucosa.

Flat active substance carriers have already been developed and produced for various purposes. DE-OS 27 46 414, which describes a film-like web of active substance, binding agent and further auxiliary substances, can be regarded as fundamental for these administration forms. Due to the homogenous thickness, density and width of the web, there is a direct correlation between a unit of length of the web and the active substance dose contained therein. The advantages of continuous dosability have also been recognized by other applicants and described in special single variants. Thus, DE-PS 36 30 603 describes a flat-shaped carrier material, e.g. in the form of a release paper provided with an active substance-containing coating, the latter being strippable from the carrier material following previous separation into dosage units.

In DE-OS 196 52 188 there is described a flat pharmaceutical preparation which is suitable for application and release of the opiate analgesic buprenorphine in the oral cavity. A disadvantage with this administration form is that a major part of the amount of active substance contained therein is transported via the saliva into the stomach and metabolised since the administration form is not mucoadhesive or insufficiently mucoadhesive.

It is true that the general advantages of flat administration forms are known in the state of the art, e.g. a more rapid active substance release and easier dosability, which have already been mentioned. Furthermore, the possibility of taking the dosage form in a discreet manner, that is, without the aid of a liquid, furthermore advantages in manufacture, and the possibility of printing on the administration form during the manufacture thereof, which results in increased safety in taking the medicine.

Despite the afore-described advantages such flat-shaped administration forms have so far been hardly successful. Presumably, many manufacturers of pharmaceutics consider the advantage over conventional administration forms to be too small, so that it appears not to be profitable to develop products of this type and to obtain approval according to the law on pharmaceutics. Especially where the active substance is orally applicable anyhow, there is a reluctance to accept the expenditure involved in the development of an alternative administration form, even if the advantages connected with this administration form are known.

A further reason why flat-shaped oral administration forms have hitherto hardly been successful is presumably insufficient patient compliance. Many active substances are characterized by a bitter taste so that oral administration thereof is accompanied by the sensation of an unpleasant taste, especially where the active agent is absorbed via the oral mucosa. This unpleasant taste sensation leads to a low acceptance of sheet-like oral administration forms with patients.

In the case of tablets and capsules which disintegrate and release the active substance in the stomach, the problems caused by the bitter taste of the active substances are generally solved by coating the administration form with a coating of neutral taste.

For thin, flat medicinal preparations which release the active substance in the oral cavity, coating of these administration forms with a coating of neutral taste is not possible. This approach to masking a taste is especially problematic with mucoadhesive and/or rapidly disintegrating flat administration forms where the active substance is to be released and absorbed by the oral mucosa as quickly as possible, or with administration forms which are applied as purely mucoadhesive systems over extended periods.

SUMMARY OF THE INVENTION

The object of the invention was therefore to provide thin, sheet-like pharmaceutical preparations for administration of active substances via the oral mucosa which no longer exhibit the disadvantages of a problematic taste sensation, or otherwise have such a disadvantage significantly reduced.

According to the invention, this object is achieved by film-shaped or wafer-shaped pharmaceutical preparations, for administering active substances which have an unpleasant taste, containing at least one matrix-forming polymer. The matrix-forming polymer comprises at least one active substance and at least one gas-forming component therein. The gas-forming component comprises at least one carbon dioxide-forming substance, without the addition of an acid, reducing or suppressing the unpleasant taste of the active substance.

The pharmaceutical preparations according to the invention comprise a matrix which is formed of at least one matrix-forming polymer and which, apart from at least one active substance, also has at least one carbon dioxide-forming agent, without the addition of an acid, dissolved or dispersed therein.

The use of carbon dioxide-forming substances has already been described in connection with medicinal chewing gums.

Thus, U.S. Pat. No. 4,639,368 states that carbon dioxide-forming substances may be contained in the base material of the chewing gum preferably as fine granules having a size of less than 10 µm.

Carbon dioxide-forming substances suitable for the pharmaceutical preparations according to the invention are pharmaceutically applicable monobasic to dibasic salts of carbonic acid, e.g. alkali metal hydrogen carbonates or alkali metal carbonates, alkali earth metal carbonates or ammonium carbonates and mixtures thereof. Other physiologically acceptable carbon dioxide-forming substances may also be utilized. Preferred carbon dioxide-releasing substances are sodium hydrogen carbonate, sodium carbonate, potassium hydrogen carbonate or potassium carbonate. Carbon dioxide-forming substances are known to those skilled in the art and may be effective when combined with each other. The carbon dioxide-forming substance is contained in the pharmaceutical preparation in an amount of 2 to 50%-wt, preferably 5 to 30%-wt, and with particular preference 7 to 20%-wt, relative to the pharmaceutical preparation.

Combined with an acid, but also without an acid, sensation of taste in the case of oral application of a pharmaceutical preparation according to the present invention which contains a carbon-dioxide-forming substance without added acid is, surprisingly, altered such that bitter-tasting substances or active agents no longer produce an unpleasant taste, or do so only to a strongly reduced degree.

The pharmaceutical preparations according to the present invention are suitable for a plurality of different active substances.

It is, however, a precondition for a transmucosal, e.g. buccal or sublingual, application in the oral cavity that, taking into consideration the required dose, the oral mucosa is sufficiently permeable to the active substance. Permeability is, in turn, highly dependent on the physicochemical properties of the active substance. In the case of pharmaceutical preparations according to the present invention which are to be swallowed it is a prerequisite that the active substances are absorbed in the stomach and/or the intestine.

Examples of active substances suitable for administration with the pharmaceutical preparation according to the invention are antipyretics and analgesics, e.g. ibuprofen, acetaminophen or aspirin; laxatives, e.g. phenolphthalein dioctyl sodium sulfosuccinate; appetite depressants, e.g. amphetamines, phenylpropanolamine, phenylpropanolamine hydrochloride or caffeine; antiacidics, e.g. calcium carbonate; anti-asthmatics, e.g. theophylline; antidiuretics, e.g. diphenoxylate hydrochloride; agents active against flatulence, e.g. simethecon; migraine agents, e.g. ergotaminetartrate; psychopharmacological agents, e.g. haloperidol; spasmolytics or sedatives, e.g. phenobarbitol (with or without atropine); antihyperkinetics, e.g. methyldopa or methylphenidat; tranquilizers, e.g. benzodiazepines, hydroxinmeprobramates or phenothiazines; antihistaminics, e.g. astemizol, chlorpheniramine maleate; pyridamine maleate, doxlamine succinate, bromopheniramine maleate, phenyltoloxamine citrate, chlorocyclizine hydrochloride, pheniramine maleate or phenindamine tartrate; decongestants, e.g. phenylpropanolamine hydrochloride, phenylephrine hydrochloride, pseudoephidrine hydrochloride, pseudoephidrine sulfate, phenylpropanolamine bitartrate or ephedrine; beta-receptor blockers, e.g. propanolol; agents for alcohol withdrawal, e.g. disulfiram; antitussives, e.g. benzocaine, dextrometorphane, dextrometophane hydrobromide, noscapine, carbetapentane citrate or chlophedianol hydrochloride; fluorine supplements, e.g. sodium fluoride; local antibiotics, e.g. tetracycline or cleocine; corticosteroid supplements, e.g. prednisone or prednisolone; agents against goiter formation, e.g. colchicine or allopurinyl; antiepileptics, e.g. phenytoine sodium; agents against dehydration, e.g. electrolyte supplements; antiseptics, e.g. cetylpyridinium chloride; non-steroidal antiphlogistic active agents (antiphlogistics), e.g. acetaminophen, ibuprofen, dexiprofenlysinate, naproxen, or salts thereof; gastrointestinal active agents, e.g. loperamide or famotidine; various alkaloids, e.g. codeine phosphate, codeine sulfate or morphine; supplements for trace elements, e.g. sodium chloride, zinc chloride, calcium carbonate, magnesium oxide or other alkali metal salts and alkali earth metal salts; vitamins; ion-exchange resins, e.g. cholestyramine; cholesterol-depressant and lipid-lowering substances; antiarrhythmics, e.g. N-acetylprocainamide; or expectorants, e.g. guaifenesin.

To be mentioned in particular are the following active agents: ketoprofen, ibuprofen, loperamide, selegiline, antipamezol, nicotine, quinine, bruzine, paracetamol, dextromethorphane, caffeine and other xanthines such as theophilines and theobromines, pyrazolones such as metamizol, magnesium sulfate, zopliclon or zolpidem.

Furthermore, pharmacologically active substances are also suitable as active agents; these are contained in the following classes or groups: α-adrenergic agonists; β-adrenergic agonists; α-adrenergic blockers; β-adrenergic blockers; alcohol withdrawal agents; aldose-reductase inhibitors; anabolics; narcotic analgesics, preferably codeine, morphine derivatives; non-narcotic analgesics, preferably salicylates and their derivatives; androgens; anaesthetics; appetite depressants; anthelmintics (active against cestodes, nematodes, Onchocerca, schistosomes or trematodes); anti-acne agents; anti-allergics, anti-amoebic agents (amoebecidal agents); anti-androgens; agents against angina pectoris; antiarrhythmics; anti-arteriosclerotic agents; anti-arthritic/antirheumatic agents; antibacterial agents (antibiotics), preferably aminoglycosides, amphenicols, ansamycines, β-lactams (especially carbapenemes, cephalosporins, cephamycines, monolactams, oxacephemes, penicillins), lincosamides, macrolides, polypeptides, tetracyclines; synthetic antibacterial agents, preferably 2,4-diaminopyrimidines, nitrofuranes, quinolones and quinolone analogues, sulfonamides, sulfones; anticholinergics; anticonvulsants; antidepressants, preferably bicyclic antidepressants, hydrazides, hydrazines, pyrrolidones, tetracyclic antidepressants; tricyclic antidepressants, polycyclic imides; antidiabetic agents, preferably biguanides, sulfonyl-urea derivatives; antidiarrhoeal agents; antidiuretics; anti-estrogens; antimycotics/fungicidal agents, preferably polyenes; synthetic antimycotics/fungicidal agents, preferably allylamines, imidazoles, triazoles; anti-glaucoma agents; antigonadotropins; agents against gout; antihistaminics, preferably alkylamine derivates, aminoalkyl ethers, ethylenediamine derivates, piperazines, tricyclic compounds (especially phenothiazines); antihyperlipoproteinaemic agents (lipid-lowering agents), preferably aryloxyalcanoic acid derivates (especially clofibrinic acid derivatives and analogues), bile acid-sequestering (masking) substances, HMG-CoA-reductase inhibitors, nicotinic acid derivatives, thyroid gland hormones and analogues thereof; anti-hypertensive/blood pressure-lowering agents, preferably benzothiadiazine derivatives, N-carboxyalkyl-(peptide/lactam) derivatives, guanidine derivatives, hydrazines/phthalazines, imidazole derivatives, quaternary ammonium compounds, quinazoline derivatives, reserpine derivatives, sulphonamide derivatives; agents against hyperthyroidism; agents against hypotension; agents against hypothyrosis; non-steroidal anti-inflammatory agents (antiphlogistics), preferably aminoaryl-carboxylic acid derivatives, arylacetic acid derivatives, arylbutyric acid derivatives, arylcarboxylic acid derivatives, arylpropionic acid derivatives, pyrazoles, pyrazolones, salicylic acid derivatives, thiazine carboxamide; antimalarial agents, preferably quinine and its salts, acids and derivatives; anti-migraine agents; agents against nausea; antineoplastic agents, preferably alkylating agents (especially alkyl sulfonates, aziridines, ethyleneimines and methylmelamines, nitrogen mustard gases, nitrosoureas), antibiotic agents, antimetabolites (especially folic acid analogues, purine analogues, pyrimidine analogues), enzymes, interferons, interleukins; hormonal antineoplastic agents, preferably androgens, anti-adrenal agents, anti-androgens, anti-estrogens (especially aromatase inhibitors); antineoplastic dietary additives; anti-Parkinson agents; agents against pheochromocytomae; agents against pneumocystis; agents for treating hypertrophy of the prostate; protozoacide agents, preferably against Leishmania, Trichomonas, Trypanosoma; antipruritic agents; antipsoriatic agents; antipsychotic agents, preferably butyrophenones, phenothiazines, thioxanthenes, other tricyclic agents, 4-arylpiperazine, 4-arylpiperidine; antipyretic agents; agents against rickettsiae; agents against seborrhoea; antiseptics, preferably guanidine, halogens and halogen compounds, nitrofuranes, phenols, quinolines; antispasmodic/spasmolytic agents; antithrombotics; antitussives; anti-ulcus agents; uricostatics (antiurolithics); antivenenum; antiviral agents, preferably purines, pyrimidinones; anxiolytics, preferably arylpiperazines, benzodiazepine derivatives, carbamates; benzodiazepine antagonists; bronchodilators, preferably ephedrine derivatives, quaternary ammonium compounds, xanthine derivatives; calcium channel blockers, preferably arylalkylamines, dihydropyridine derivatives, piperazine derivatives; calcium regulators; cardiotonics; chelate or complex formers; cholecystokinine antagonists; cholelitholytic agents; choleretics; cholinergics; cholinesterase inhibitors; cholinesterase reactivators; CNS stimulants; decongestion agents; prophylactic agents against dental caries; depigmenting agents; diuretics, preferably organic mercury compounds, pteridines, purines, steroids, sulphonamide derivatives, uracils; dopamine receptor agonists; agents against ectoparasites; enzymes, preferably digestive enzymes, penicillin-inactivating enzymes, proteolytic enzymes; enzyme-inducing agents; steroidal and non-steroidal estrogens; gastric secretion inhibitors; glucocorticoids; gonad-stimulating active agents; gonadotropic hormones; growth hormone inhibitors; growth hormone-releasing factor; growth stimulants; haemolytic agents; heparin antagonists; hepatoprotective agents, agents for treating diseases of the liver; immunomodulatores; immunosuppressing agents; ion exchange resins; lactation-stimulating hormones; LH-RH agonisten; lipotropic agents; agents against lupus erythematosus; mineralocorticoids; miotics; monoaminoxidase inhibitors; mucolytics; muscle relaxants; narcotics antagonists; neuroprotective agents; nootropics; ophthalmics; ovarian hormones; oxytozics; pepsin-inhibitors; peristaltic stimulants; progestogens; prolactin inhibitors; prostaglandins and prostaglandin analogues; protease inhibitors; respiratory stimulants; sclerosing agents; sedatives/hypnotics, preferably acyclic ureides, alcohols, amides, barbituric acid derivatives, benzodiazepine derivatives, bromides, carbamates, chloral derivatives, piperidinediones, quinazolone derivatives; thrombolytics; thyreotropic hormones; uricosurics; vasodilators (cerebral); vasodilators (coronary); vasodilators (peripheral); vasoprotective agents; vitamins, vitamin precursors, vitamin extracts, vitamin derivatives; vulneraries.

Active substances which have a particularly unpleasant taste are antibacterial agents based on pyridonecarboxylic acid, with 5-amino-1-cyclopropyl-6,8-difluoro-7-(cis-3,5-dimethyl-1-piperazinyl)-1,4-dihydro-4-oxoquinolone-3-carboxylic acid being regarded as particularly unpleasant, enoxacine, pipemdic acid, ciprofloxacin, ofloxacin and pefloxacin, antiepileptics such as zonisamide, macrolide antibiotics such as erythromycin, beta-lactam antibiotics such as penicillins or cephalosporins, psychotropic active substances such as chlorpromazine, active substances such as sulpyrine, or agents active against ulcers, such as cimetidine.

The above list of active substances that according to the present invention can be administered with the administration form is not complete. The present invention also encompasses preparations containing a combination of one or more active substances. Such a preparation can be of advantage in various respects since it is possible to incorporate any therapeutically useful active agent in the preparation according to the invention.

This means that several concomitant symptoms or conditions can be treated by means of a fixed active substance combination in a single medicament.

To support the active substance uptake via the oral mucosa, a preferred embodiment provides for the addition of agents which accelerate the uptake of active agent (permeation enhancers). Suitable permeation enhancers are, in particular: propanediol, dexpanthenol, oleic acid; the enhancer(s) may, for example, be selected from the following group: saturated or unsaturated fatty acids, hydrocarbons, straight-chain or branched fatty alcohols, dimethyl sulfoxide, propylene glycol, decanol, dodecanol, 2-octyldodecanol, glycerol, isopropylidene glycerol, transcutol (=diethyleneglycol-monoethyl ether), DEET (=N,N-diethyl-m-tolueneamide), solketal, ethanol or other alcohols, menthol and other essential oils or components of essential oils, lauric acid diethanolamide, D-alpha-toco-pherol and dexpanthenol; the above list is not complete.

Combinations of two or more enhancer substances can also be used.

The uptake of active substance can furthermore be improved by means of substances stimulating the blood flow which can be added to the preparations according to the invention. Among these are, in particular: menthol, eucalyptol, ginkgo extract, geranium oil, camphor, spearmint oil, oil of juniper and rosemary. These blood flow-stimulating substances may be used singly or in combination with one or more of the afore-mentioned permeation-enhancing substances.

DESCRIPTION OF THE INVENTION

According to a particular embodiment of the present invention, the inventive film-shaped or wafer-shaped pharmaceutical preparations are capable of disintegrating. They can be configured, for example, as quickly disintegrating administration forms, i.e. administration forms disintegrating within a period of 1 second up to 3 minutes, or as slowly disintegrating administration forms, i.e. administration forms disintegrating within a period of 3 to 15 minutes. But administration forms which can be sucked also represent a subject matter of the present invention.

Systems which are mucoadhesive but do not disintegrate or erode, or do so very slowly, must be removed after the active substance has been released. The retention time of these systems can be up to several hours.

The disintegration process should substantially be completed within 15 min if the medicament form adhering to the oral mucosa was surrounded during this period by an aqueous medium, e.g. a body fluid. According to preferred embodiments of the invention, the pharmaceutical forms are configured such that they disintegrate within 3 min, and particularly within 60 seconds, after introduction in an aqueous medium.

The disintegration times indicated are based on the measurement of disintegration times according to Pharm. Eur. 2.9.1 "Zerfallszeiten von Tabletten und Kapseln" [Disintegration Times of Tablets and Capsules].

The indicated disintegration times can be set to the above-mentioned ranges by using matrix-forming polymers which have different disintegrating, respectively solubility characteristics. A pharmaceutical preparation based on polyvinyl alcohol, for example, will disintegrate much more quickly than a medicinal HPMC preparation. Thus, by mixing the corresponding polymer components, the disintegration time can be adjusted. In addition, disintegrants are known which "draw" water into the matrix and cause the matrix to burst open from within. As a consequence, it is also possible to add such disintegrants for the purpose of adjusting the disintegration time.

The matrix of the inventive, quickly disintegrating administration forms contains as base materials a water-soluble polymer, or mixtures of such polymers. Synthetic or partially synthetic polymers or biopolymers of natural origin which are film-forming and water-soluble are preferably used for this purpose. Especially suitable are polymers which are preferably selected from the group comprising cellulose derivatives, polyvinyl alcohol (e.g. MOWIOL®), polyacrylates and polyvinyl pyrrolidone.

Of the cellulose derivatives hydroxypropylmethyl cellulose, carboxymethyl cellulose, sodium-carboxymethyl cellulose (e.g. Walocel), hydroxyethyl cellulose, hydroxypropyl cellulose and methyl cellulose are particularly preferred. Also preferred are water-soluble polysaccharides of plant or microbial origin, especially pullulan, xanthan, alginates, dextranes and pectins. Furthermore, proteins, preferably gelatine or other gel-forming proteins are suitable. In addition, starch and starch derivatives; gelatine (various types); polyvinyl pyrrolidone; gum arabic; pullulan; acrylates; polyethylene oxide, especially the Polyox 10, Polyox 80, Polyox 205, Polyox 301, Polyox 750 types (Union Carbide); copolymers of methylvinyl ether and maleic acid anhydride (Gantrez-Copolymers, especially the ES, MS and S types; ISP Global Technologies GmbH).

For the structure of a matrix which releases the active substance slowly, the polymers used with preference are those selected from the group comprising cellulose ethers, preferably ethyl cellulose, as well as polyvinyl alcohol, polyurethane, polymethacrylates, polymethyl methacrylates and derivatives and copolymerisates of the aforementioned polymers.

The polymer film's poor solubility or insolubility in aqueous medium, or its water-resistant configuration, results in the active substance release taking place only slowly by way of diffusion and—given a suitable formulation—with a slow diffusion coefficient. This leads to a slow release of active substance.

To reduce the solubility, respectively the release rate, of the slow-release layer(s), the polymer layer may be subjected to annealing. Thus, a highly hydrolysed polyvinyl alcohol, for example, may be used as a base polymer for the insoluble, slow-releasing layer if said alcohol is rendered insoluble by annealing.

With the preparations according to the present invention, the active substance release takes place by way of permeation through the oral mucosa. As a prerequisite for this, the flat preparation must be in close contact with the mucosa during the period of application, i.e. if possible until the dissolution or disintegration of the preparation has taken place. By choosing suitable auxiliary substances, it is possible to produce improved contact between the inventive pharmaceutical preparation and the oral mucosa. For this reason, the pharmaceutical preparation according to a preferred embodiment of the invention contains an adhesion-imparting auxiliary substance or auxiliary substance mixture imparting bio-adhesive or mucoadhesive properties to the preparation. Certain orally applicable auxiliary substances which are usual in pharmaceutics are known to possess mucoadhesive properties. Examples for such mucoadhesive substances are polyacrylic acid, carboxymethyl cellulose, hydroxymethyl cellulose, methyl cellulose, tragacanth, alginic acid, gelatine and gum arabic. Furthermore, various non-mucoadhesive substances are known also to develop mucoadhesive properties in certain mixing ratios. An example for such a mixture is glycerol mono-oleate/water with a ratio of 84:16 (Engström et al., Pharm. Tech. Eur. 7 [1995], No. 2, p. 14-17).

When using bio-adhesive or mucoadhesive auxiliary substances, a bilayer or multilayer structure of the administration form of the inventive preparation is to be preferred. Because of the fact that only the layer or layers which is/are facing, respectively are in contact with, the oral mucosa is/are rendered mucoadhesive, but not the distal or outwardly located layer or layers, it is possible to avoid that the preparation, during the period of application, causes different parts of the mucosa to stick together, which would lead to considerable unpleasant sensations in use. Preferred embodiments are therefore bilayer or multilayer, with one of the two layers, or in the case of a multilayer structure one of the layers, having mucoadhesive properties. This structure is preferred for non-disintegrating or only very slowly disintegrating or eroding systems.

In the case of embodiments which apart from mucoadhesive layers also contain non-mucoadhesive layers, the latter are preferably configured such that their permeability for the active substance is lower than that of the bio-adhesive or mucoadhesive layer. In this way, the active substance can be prevented from being released into the saliva of the oral cavity, which would lead to loss of active substance.

The mentioned pharmaceutical preparations are comparatively dense structures preferably having a density between 0.3 $g/cm^3$ and 1.7 $g/cm^3$, especially preferably between 0.5 $g/cm^3$ and 1.5 $g/cm^3$, and most preferably between 0.7 $g/cm^3$ and 1.3 $g/cm^3$.

The total thickness of the preparations according to the invention is preferably 5 µm up to 10 mm, preferably 30 µm to 2 mm, and with particular preference 0.1 mm to 1 mm. The pharmaceutical preparations may advantageously be of round, oval, elliptic, triangular, quadrangular or polygonal shape, but they may also have any rounded shape.

The surface of the preparations according to the invention is usually smooth; it may, however, be of advantage to provide the surface with elevations and deepenings, e.g. in the form of knobs or grooves.

The invention also includes preparations of the kind mentioned herein which are present in the form of thin, solid foams. Wafers in the form of thin foams are advantageous since they quickly adhere to the mucosa due to their large specific surface, and since they also disintegrate quickly. The density of these solidified foams is preferably between 0.01 $g/cm^3$ and 0.8 $g/cm^3$, with particular preference between 0.08 $g/cm^3$ and 0.4 $g/cm^3$, and with greatest preference between 0.1 $g/cm^3$ and 0.3 $g/cm^3$. When calculating the density, the volume filled or enclosed by the entire foam body is taken as the basis for calculation.

The above-mentioned foams may be produced by introducing and dispersing gases with the aid of special foam beating devices, or by dissolving gas under pressure and subsequent relaxation of the solution.

The matrix of the inventive medicinal preparations has at least one matrix-forming polymer. The matrix-forming polymer(s) constitute(s) a substantial component of the matrix; the polymer portion amounts to at least 3%-wt. and maximally 98%-wt., preferably 7 to 80%-wt., with particular preference 20 to 50%-wt., each value being relative to the entire preparation. The mucoadhesive properties as well as the disintegration properties are determined substantially by the type of the matrix-forming polymer(s), as well as by the relative proportions of these polymers in the preparation.

To further reduce the adhesion tendency of the administration forms, it is also possible for the surfaces of the administration form to be of uneven or irregular shape, preferably undulatory or relief-like. Such an irregular surface structure may be caused, for example, by the bubble-shaped cavities which are introduced in the polymer matrix.

Apart from the matrix-forming polymers, auxiliaries may optionally be added to the matrix. For this purpose the following are taken into consideration: fillers (e.g. $SiO_2$); dyes and pigments (e.g. quinoline yellow or $TiO_2$); disintegrants, especially disintegrants which draw water into the matrix and which burst the matrix from within (e.g. aerosil); emulsifiers (e.g. polyethoxylated sorbitan fatty acid esters such as TWEEN® or polyethoxylated fatty alcohols such as BRIJ®); plasticizers (e.g. polyethylene glycol, glycerol); sweeteners (e.g. aspartame, saccharin); preserving agents (e.g. sorbic acid and its salts), and flavouring agents.

Furthermore, stabilisers or antioxidants may also be added as auxiliaries, such as, for example, ascorbyl palmitate, sodium disulfite, vitamin E, vitamin A, vitamin C; both singly and in combination with each other, or in combination with other auxiliaries.

According to a preferred embodiment, the preparations according to the invention contain at least one flavouring substance and/or at least one sweetener and/or at least one plasticizer.

The composition of the preparations according to the invention will be illustrated by way of example with reference to the following recipes, without thereby limiting the scope of the invention:

EXAMPLE

|  | Example 1 | Example 2 |
|---|---|---|
| Metolose 60 SH 50 | 45.0 | 45.0 |
| Aspartame | 10.0 | 10.0 |
| Mannitol | 10.0 | 10.0 |
| Menthol | 5.0 | 5.0 |
| Flavouring | 10.0 | 5.0 |
| Titanium dioxide | — | 5.0 |
| Sodium hydrogencarbonate | 10.0 | 10.0 |
| Loperamide | 10.0 | 10.0 |

In a taste testing it was shown that addition of 10%-wt of sodium hydrogencarbonate, corresponding to 2.0 mg/wafer, leads to the complete disappearance of the sensation of the bitter taste of loperamide.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A method for orally administering a film-shaped or wafer-shaped pharmaceutical mucoadhesive preparation the preparation being not capable of disintegrating in an aqueous medium, and the preparation containing at least one matrix-forming polymer comprising both at least one active substance having an unpleasant taste and at least one carbon dioxide forming substance which is not combined with an acid, wherein said unpleasant taste of said at least one active substance is reduced or suppressed, said method comprising the steps of:

providing said pharmaceutical preparation which contains the at least one matrix-forming polymer comprising the at least one unpleasant taste active substance and the at least one carbon dioxide forming substance dissolved or dispersed therein, wherein said at least one carbon dioxide forming substance which is not combined with an acid;

applying said preparation to a surface of the oral mucosa of a human or animal organism; and removing the preparation from the oral mucosa of a human or animal organism after the active substance has been released.

2. The method according to claim 1, wherein the at least one carbon dioxide-forming substance is selected from the group consisting of sodium hydrogencarbonate, sodium carbonate, potassium carbonate and potassium hydrogen carbonate.

3. The method according to claim 1, wherein the preparation contains said at least one carbon dioxide-forming substance in an amount of 2 to 50%-wt relative to the pharmaceutical preparation.

4. The method according to claim 3 wherein the preparation contains said at least one carbon dioxide-forming substance in an amount of 5 to 30%-wt relative to the pharmaceutical preparation.

5. The method according to claim 4 wherein the preparation contains said at least one carbon dioxide-forming substance in an amount of 7 to 20%-wt relative to the pharmaceutical preparation.

6. The method according to claim 1, wherein the preparation further comprises at least one additional substance selected from the group consisting of at least one permeation enhancer and at least one blood flow stimulator.

7. The method according to claim 6, wherein the at least one permeation enhancer is selected from the group consisting of saturated fatty acids, unsaturated fatty acids, hydrocarbons, straight-chain or branched fatty alcohols, dimethyl sulfoxide, propylene glycol, decanol, dodecanol, 2-octyldodecanol, glycerol, isopropylidene glycerol, transcutol (=diethyleneglycol-monoethyl ether), DEBT (N,N-diethyl-m-tolueneamide), solketal, ethanol or other alcohols, menthol and other essential oils or components of essential oils, lauric acid diethanolamide, D-alpha-tocopherol and dexpanthenol.

8. The method according to claim 6, wherein the at least one blood flow stimulator is selected from the group consisting of menthol, eucalyptol, ginkgo extract, geranium oil, camphor, spearmint oil, oil of juniper, and rosemary.

9. The method according to claim 1, wherein the at least one matrix-forming polymer is selected from the group consisting of cellulose ether, polyvinyl alcohol, polyurethane, polymethacrylate, polymethyl methacrylate and derivatives and copolymerisates of each of said polymers.

10. The method according to claim 9, wherein the cellulose ether is ethyl cellulose.

11. The method according to claim 1, wherein the pharmaceutical preparation further comprises an auxiliary substance for imparting mucoadhesive properties to the preparation.

12. The method according to claim 11, wherein the pharmaceutical preparation includes a bilayer or multilayer structure having at least one layer in contact with the oral mucosa of a human or animal organism, wherein the at least one layer in contact with the oral mucosa is mucoadhesive, and at least one non-mucoadhesive layer.

13. The method according to claim 12, wherein the at least one non-mucoadhesive layer has a lower permeability for said at least one active substance.

14. The method according to claim 1, wherein the preparation is flat-shaped having a density between 0.3 g/cm$^3$ and 1.7 g/cm$^3$.

15. The method according to claim 14, wherein the preparation has a density between 0.5 g/cm$^3$ and 1.5 g/cm$^3$.

16. The method according to claim 15, wherein the preparation has a density between 0.7 g/cm$^3$ and 1.3 g/cm$^3$.

17. The method according to claim 1, wherein the total thickness of the preparation is 5 μm to 10 mm.

18. The method according to claim 17, wherein the total thickness of the preparation is 30 μm to 2 mm.

19. The method according to claim 18, wherein the total thickness of the preparation is 0.1 mm to 1 mm.

20. The method according to claim 1, wherein the preparation has a shape selected from the group consisting of round, ellipsoid, oval, triangular, quadrangular polygonal, and irregular rounded.

21. The method according to claim 1, wherein the preparation is present as a solidified foam having a density between 0.01 g/cm$^3$ and 0.8 g/cm$^3$.

22. The method according to claim 21, wherein the solidified foam has a density between 0.08 g/cm$^3$ and 0.4 g/cm$^3$.

23. The method according to claim 22, wherein the solidified foam has a density between 0.1 g/cm$^3$ and 0.3 g/cm$^3$.

24. The method according to claim 1, wherein the polymer portion of the matrix has a weight at least between 3%-wt. and 98%-wt relative to the entire preparation.

25. The method according to claim 24, wherein the polymer portion of the matrix has a weight at least between 7 to 80%-wt. relative to the entire preparation.

26. The method according to claim 25, wherein the polymer portion of the matrix has a weight at least between 20 to 50%-wt. relative to the entire preparation.

27. The method according to claim 1, wherein the preparation further comprises at least one additional auxiliary substance selected from the group consisting of fillers, colourants, disintegrants, emulsifiers, plasticizers, sweeteners, preserving agents, stabilisers, antioxidants and flavouring agents.

28. The method according to claim 1, wherein the preparation further comprises at least one flavouring agent, at least one sweetener, or at least one plasticizer.

* * * * *